United States Patent
Lizio et al.

(10) Patent No.: US 7,871,643 B2
(45) Date of Patent: Jan. 18, 2011

(54) PHARMACEUTICAL FORM HAVING A TWO-LAYER SEPARATING LAYER

(75) Inventors: Rosario Lizio, Rossdorf (DE); Erna Roth, Darmstadt (DE); Hans-Ulrich Petereit, Darmstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 149 days.

(21) Appl. No.: 11/780,915

(22) Filed: Jul. 20, 2007

(65) Prior Publication Data

US 2008/0026051 A1  Jan. 31, 2008

Related U.S. Application Data

(60) Provisional application No. 60/908,855, filed on Mar. 29, 2007.

(30) Foreign Application Priority Data

Jul. 27, 2006  (DE)  ........................ 10 2006 035 549

(51) Int. Cl.
A61K 9/14 (2006.01)
A61K 9/20 (2006.01)
A61K 9/28 (2006.01)
A61K 9/48 (2006.01)
A61P 43/00 (2006.01)

(52) U.S. Cl. ........................ 424/452; 424/465; 424/486; 427/2.16

(58) Field of Classification Search ........................ None
See application file for complete search history.

(56) References Cited

U.S. PATENT DOCUMENTS

2005/0208133 A1* 9/2005 Tsutsumi et al. ............ 424/472
2006/0210630 A1* 9/2006 Liang et al. .................. 424/468
2006/0269605 A1 11/2006 Lizio et al.
2007/0026082 A1 2/2007 Lizio et al.
2007/0042045 A1 2/2007 Lizio et al.
2008/0044470 A1 2/2008 Petereit et al.
2008/0166416 A1 7/2008 Lizio et al.
2009/0041842 A1* 2/2009 Lizio et al. .................. 424/466

FOREIGN PATENT DOCUMENTS

| EP | 1614413 A2 | 1/2006 |
| EP | 1614413 A3 | 1/2006 |
| EP | 1728512 A1 | 12/2006 |
| WO | WO 2005/027890 A1 | 3/2005 |
| WO | WO 2006/085335 A2 | 8/2006 |
| WO | WO 2006/085335 A3 | 8/2006 |

OTHER PUBLICATIONS

U.S. Appl. No. 11/815,632, filed Aug. 6, 2007, Lizio, et al.
U.S. Appl. No. 60/908,855, filed Mar. 29, 2007, Lizio, et al.
U.S. Appl. No. 11/994,440, filed Jan. 2, 2008, Petereit, et al.
U.S. Appl. No. 11/721,399, filed Jun. 11, 2007, Lizio, et al.
U.S. Appl. No. 12/598,138, filed Oct. 29, 2009, Liu, et al.

* cited by examiner

*Primary Examiner*—Shanon A Foley
*Assistant Examiner*—Sarah Al-Awadi
(74) *Attorney, Agent, or Firm*—Oblon, Spivak, McClelland, Maier & Neustadt, L.L.P.

(57) ABSTRACT

A pharmaceutical form, contains an active compound-containing core, which is covered with a coating layer of a gastric juice-resistant, intestinal juice-soluble (meth)acrylate copolymer, a separating layer situated between said core and said coating layer, the separating layer containing a film-forming water-soluble polymer, wherein the separating layer contains at least two layers: an inner layer containing a water-repellent substance, and thereon a layer comprising the film-forming water-soluble polymer.

27 Claims, No Drawings

PHARMACEUTICAL FORM HAVING A TWO-LAYER SEPARATING LAYER

BACKGROUND OF THE INVENTION

1. Field of the Invention

The invention relates to a pharmaceutical form having a separating layer.

2. Description of the Related Art

EP 0 088 951 A2 describes a process for the coating of pharmaceutical forms by means of a coating agent dispersed in water. For the redispersion of carboxyl group-containing (meth)acrylate copolymers from powders to give dispersions, the partial neutralization of the carboxyl groups is recommended. Salt formation of the acidic groups takes place by reaction with a base. Suitable bases are alkalis, such as, for example, sodium hydroxide solution, potassium hydroxide solution, soda, potash, sodium bicarbonate, trisodium phosphate, trisodium citrate or ammonia or physiologically tolerable amines, such as triethanolamine or tris(hydroxymethyl)aminomethane. A degree of neutralization of 0.1 to 10% by weight of the carboxyl groups contained in the copolymer is favourable with respect to redispersion.

WO 2004/096185 describes a pharmaceutical form and a process for its production. The pharmaceutical form is coated with an anionic (meth)acrylate copolymer which can be partially neutralized if required. In order to prepare a solution of the anionic copolymer, a partial or complete neutralization of the acid groups is usually necessary. The anionic copolymer can, for example, gradually be stirred into water in a final concentration of 1 to 40% by weight and can be partially or completely neutralized in the course of this by addition of a basic substance such as, for example, NaOH, KOH, ammonium hydroxide or organic bases such as, for example, triethanolamine. It is also possible to employ a powder of the copolymer, to which a base, for example NaOH, has already been added during its preparation for the purpose of (partial) neutralization, such that the powder is an already (partially) neutralized polymer. The pH of the solution is usually over 4, e.g. in the range from 4 to about 7.

WO 2005/007139 describes multiparticulate pharmaceutical forms, comprising mucoadhesively formulated peptide or protein active compounds. The application mentions that a separating layer can be applied between active compound-containing and intestine-soluble copolymer layer, which serves for the separation of active compound and coating material for the purpose of the prevention of interactions. This layer can consist of inert film-forming agents (e.g. HPMC, HPC or (meth)acrylic acid copolymers) or, for example, talc or another suitable pharmaceutical substance. Likewise, combinations of film-forming agents and talc or similar substances can be used. It is also possible to apply a separating layer of partially or completely neutralized (meth)acrylate copolymer dispersions. The separating layer can consist of the same or another mucoadhesive polymer as in the underlying matrix layer. Possible interactions or incompatibilities of the active compound or of the mucoadhesive polymer with the film-forming (meth)acrylate copolymer layer can be encountered in this way.

It has been attempted in the case of an intestinal juice-soluble coated pharmaceutical form to achieve a high reproducibility of the active compound release, in that on reaching specific pH coatings dissolving as rapidly as possible developed. However, the present invention starts out from an alternative concept.

SUMMARY OF THE INVENTION

It is an object of the present invention to provide an intestinal juice-soluble coated pharmaceutical form in which the surrounding polymer shell is first at least approximately completely dissolved or detached, before the release of active compound commences.

This and other objects have been achieved by the present invention the first embodiment of which includes a pharmaceutical form, comprising:

an active compound-containing core, which is covered with a coating layer of a gastric juice-resistant, intestinal juice-soluble (meth)acrylate copolymer, a separating layer situated between said core and said coating layer, said separating layer comprising a film-forming water-soluble polymer, wherein the separating layer comprises at least two layers:

an inner layer containing a water-repellent substance, and thereon a layer comprising the film-forming water-soluble polymer.

DETAILED DESCRIPTION OF THE PREFERRED EMBODIMENTS

The inventors of the present invention have found that in the case of pharmaceutical forms which are provided with intestinal juice-soluble (meth)acrylate copolymer coatings, permanent interactions take place between the already escaping active compound and optionally present substances assigned to the active compound and the polymer layer additionally included in the dissolution. This interaction in principle counteracts the reproducibility of the release of active compound. With the aid of scanning electron microscopic images of coated pellets which are removed from intestinal juice at a point in time at which the release of active compound has already commenced, it can be observed that the surrounding polymer layer has usually still not dissolved or only partially dissolved from the core of the pharmaceutical form. This effect influences the release of active compound, since a part of the active compound escapes more or less unhindered locally, while other parts first have to penetrate through the remains of the surrounding shell. Since the parameters change here in a virtually uncontrolled manner, this runs contrary to an optimally controlled release of active compound with high reproducibility. According to one embodiment of the present invention, therefore, an intestinal juice-soluble coated pharmaceutical form should be provided in which the surrounding polymer shell is first at least approximately completely dissolved or detached, before the release of active compound commences as immediately as possible thereafter.

One object of the present invention is achieved by a pharmaceutical form, comprising an active compound-containing core, which is covered with a coating layer of a gastric juice-resistant, intestinal juice-soluble (meth)acrylate copolymer, where between the core and the covering layer is situated a separating layer, comprising a film-forming water-soluble polymer, wherein the separating layer is designed to be at least two-layer, an inner layer containing a water-repellent substance and thereon a layer containing the film-forming water-soluble polymer being present.

Active Compound-Containing Core

The pharmaceutical form has an active compound-containing core.

The core usually contains 5 to 100, preferably 10 to 50, % by weight of active compound, and up to 95, preferably 50 to 90, % by weight of further pharmaceutical excipients. The amount of active includes all values and subvalues therebetween, especially including 10, 20, 30, 40, 50, 60, 70, 80, and 90% by weight. The amount of excipient includes all values and subvalues therebetween, especially including 5, 10, 20, 30, 40, 50, 60, 70, 80, and 90% by weight.

Active compound-containing cores can be obtained by customary production processes such as direct compression, compression of dry, moist or sintered granules, extrusion and subsequent rounding, moist or dry granulation or by direct pelleting (e.g. on plates) or by binding of powders (powder layering) to active compound-free beads (nonpareils) or active compound-containing particles, e.g. active compound crystals.

Further pharmaceutical excipients which the cores can contain in addition to the active compound are, for example: binders such as cellulose and its derivatives, polyvinylpyrrolidone (PVP), moisturizing agents, disintegration promoters, lubricants, disintegrants, (meth)acrylates, starch and its derivatives, sugar solubilizers or other pharmaceutically customary excipients.

At Least Two-Layer Separating Layer

Between the core and the coating layer is situated a separating layer, which is designed to be at least two-layer, an inner layer containing a water-repellent substance and thereon a layer containing the film-forming water-soluble polymer being present.

The inner layer containing the water-repellent substance is in this case adjacent to the active compound-containing core. The layer containing the film-forming water-soluble polymer lies thereon or thereover and is adjacent to the outer polymer coating.

Preferably, between the core and the coating layer is situated a separating layer which is designed to be three-layer, two layers of a film-forming, water-soluble polymer enclosing a layer containing a water-repellent substance.

Usually and for function, it is adequate to design the separating layer to be two- or three-layer. In principle, it is also possible or conceivable to add further layers, e.g. further layers of the film-forming, water-soluble polymer and layers enclosed therein containing a water-repellent substance, without adversely affecting the function of the separating layer as such.

A three-layer separating layer in particular has the function of slowing the escape of the active compound until the outer polymer shell has dissolved or detached. The layer containing a water-repellent substance enclosed between two layers of a film-forming, water-soluble polymer here separates, at least for a certain time, the active compound from the outer aqueous environment, which should contribute to the desired delay of the release of active compound.

The two-, three- or optionally more than three-layer construction of the separating layer has the advantage that the polymer coating completely dissolves in more than 95% of the pellets, before the release of active compound commences with a slight delay. The complete dissolution of the polymer coating can be demonstrated by means of scanning electron microscopic images (SEM) of pellets, in which the release of active compound has just commenced in the in-vitro release experiment. Two layers of in each case 3-15% by weight of HPMC with an intermediate layer of 3-15% by weight of capric acid are preferred, in each case based on the weight of the active compound-containing core.

Film-Forming, Water-Soluble Polymer

The film-forming, water-soluble polymer is preferably particularly highly and rapidly water-soluble, which favours the dissolution or the detachment of the coating layer. The action of the layer of the film-forming, water-soluble polymer is therefore designed on this short-term action.

The film-forming, water-soluble polymer can comprise non-ionic cellulose derivatives, such as hydroxypropylcellulose, hydroxypropylmethylcellulose (HPMC), and sodium carboxymethylcellulose, polysaccharides, such as starch, amylose, alginate, pectin, xanthan and gelatins, polyethylene glycols and/or polyvinylpyrrolidone.

The water-soluble polymer can particularly preferably be a hydroxypropylmethylcellulose having a viscosity of 1 to 20, preferably 2 to 10, particularly preferably 4 to 8, mPa·s, based on a 1% strength solution (weight/weight, measurable, for example, according to Pharm. Eur 5.0, Method 2.2.10, rotary viscometer); Methocel® E5, for example, is suitable. The viscosity includes all values and subvalues therebetween, especially including 2, 4, 6, 8, 10, 12, 14, 16 and 18 mPa·s.

The layers of the film-forming, water-soluble polymer can in each case make up 1 to 50, preferably 2 to 12, preferably 3 to 8, % by weight based on the weight of the active compound-containing core. The amount layers of the film-forming, water-soluble polymer includes all values and subvalues therebetween, especially including 5, 10, 15, 20, 25, 30, 35, 40 and 45% by weight based on the weight of the active compound-containing core.

The film-forming, water-soluble polymer can have a solubility in demineralized (dem.) water of at least 50 g/l at 20° C. (water solubility according to standard methods, such as, for example, Pharmeuropa—Technical Guide for the Elaboration of Monographs, 3rd Edition (1999), Chapter IV, Appendix IV, with vigorous shaking for 1 min, allow to stand for 15 min at 20° C. in purified water).

Water-Repellent Substance

The water-repellent substance preferably forms a layer rapidly detaching from the core in micellar form under physiological conditions from pH 5.5. The detachment in micellar form, however, takes place only after the dissolution of the layer situated above containing the film-forming, water-soluble polymer, if contact with the surrounding medium is made. The layer containing the water-repellent substance is therefore designed for a short-term action, in which the escape of the active compound is slow. Usually, the water-repellent substance is not a polymer.

The water-repellent substance can in particular be a $C_8$- to $C_{24}$-fatty alcohol, an ester of $C_8$- to $C_{24}$-fatty alcohols with organic acids, a $C_8$- to $C_{24}$-fatty acid, such as, for example, stearic acid or capric acid, an ester of $C_8$- to $C_{24}$-fatty acids with alcohols or polyalcohols, such as, for example, glycerol monostearate or glycerol distearate. Substances having a melting point according to Ger. Ph. (German pharmacopoeia) in the range from 30 to 40° C. are particularly preferred.

The layer containing the water-repellent substance can make up 0.1 to 25, preferably 1 to 10, particularly preferably 3 to 8, % by weight based on the weight of the active compound-containing core. The amount of the layer containing the water-repellent substance includes all values and subvalues therebetween, especially including 0.5, 1, 5, 10, 15% by weight based on the weight of the active compound-containing core.

The water-repellent substance can have a solubility in acetone of at least 50 g/l at 20° C. (solubility in acetone according to standard methods, such as, for example, Pharmeuropa—Technical Guide for the Elaboration of Monographs, 3rd Edition (1999), Chapter IV, Appendix IV, with vigorous shaking for 1 min, allow to stand at 20° C. for 15 min in acetone).

Pharmaceutical Form Containing a Substance Assigned to the Active Compound, Promoting the Administration of the Active Compound The at least two-layer separating layer leads to a further aspect of the invention.

The invention thus also relates to a pharmaceutical form, comprising a core, and a gastric juice-resistant, intestinal juice-soluble polymer coating covering the core, the core containing an active compound and a substance assigned to the active compound promoting the administration of the active compound, between the core and the coating layer being situated a separating layer, comprising a film-forming water-soluble polymer, characterized in that the separating layer is designed to be at least two-layer, an inner layer containing a water-repellent substance and thereon a layer containing the film-forming water-soluble polymer being present.

A three-layer separating layer is preferably present, which is composed of two layers of a water-soluble, polymeric film-forming agent containing an intermediate layer of a hydrophobic substance.

"Assigned" is to be understood as meaning that the substance is intended for promoting the administration of the active compound actually contained and is therefore an indispensable constituent of the pharmaceutical form for achieving the desired therapeutic effect. Usually, the substance is present in the immediate surroundings of the active compound and can, for example, be embedded together with this in a common matrix, which optionally can additionally contain further assigned substances or further pharmaceutical excipients.

The invention can be used particularly advantageously if the active compound contained is a peptide, a protein, a nucleic acid or a polysaccharide, e.g. heparin, or a derivative of the substance classes mentioned and is combined with an assigned substance promoting the administration of the active compound (see WO 2005/007139, WO 2006/061069). Precisely in these cases, an extremely high reproducibility of the active compound release is often required (see WO 2005/007139, WO 2006/061069).

The substance assigned to the active compound can preferably be a penetration promoter and/or or a mucoadhesive polymer. The substance assigned to the active compound can furthermore be a substance which inhibits the enzymatic degradation of the active compound by enzymes occurring in the digestive tract. The substance assigned to the active compound can furthermore also be an efflux pump inhibitor (Pgp inhibitor).

Examples of penetration promoters are aminoalkyl(meth) acrylate copolymers such as, for example, Eudragit® E100 or Eudragit® E PO (see EP 1 302 201 A1). Suitable penetration promoters are in particular plasticizers such as, for example, triethyl citrate, acetyltriethyl citrate, diethyl sebacate, dibutyl sebacate, polymers such as carbomer, chitosan, chitosan-cysteine, sodium carboxymethylcellulose, N-trimethylated chitosan, polycarbophilic cysteines, long-chain fatty acids, their esters (for example mono- and diglycerides) and their salts such as lauric acid, laurylsulphonic acid, palmitic acid, caprylic acid, capric acid, oleic acid, acylcarnitines, chelating agents such as EDTA, salicylates, cyclodextrins, polyacrylic acids, bile acids such as cholic acid, cholyltaurine, cholylsarcosine, chenodeoxycholic acid and its salts such as Na cholate, Na glycocholate, Na taurocholate, Na taurodihydrofusidate, Na glycodihydrofusidate, surfactants and emulsifiers such as in particular polyethylene 660 12-hydroxystearate (Solutol® HS15) (Solutol HS15), polysorbate 80 (Tween 80), polyoxyethylated castor oil (Cremophor EL), polyoxyethylene-polyoxypropylene glycol (Pluronic© F68), the toxin Zonula occludens toxin (ZOT) and vitamins such as vitamin E (tocopherol) and its derivatives or vitamin B12.

Examples of polymers having mucoadhesive action are in particular chitosans (chitosan and derivatives, chitosans), (meth)acrylate copolymers, consisting of 20-45% by weight of methyl methacrylate and 55 to 80% by weight of methacrylic acid, celluloses having mucoadhesive action, in particular methylcelluloses, such as Na carboxymethylcellulose (e.g. Blanose®).

Examples of enzyme inhibitors are the Bowman Birk inhibitor (see US 2004/0219216 A1) additives of acids (EP 0 929 270 B1, U.S. Pat. No. 6,086,918) or aminoalkyl (meth) acrylate copolymers such as, for example, Eudragit® E100 or Eudragit® E PO (see EP 1 466 626 A1). Pharmaceutically suitable protease inhibitors are, for example, antipain, aprotinin, bacitracin, benzamidine, bestatin, captopril, chymostatin, chicken ovoinhibitor, EDTA-$Na_2$, chitosan-EDTA conjugates, Na glycocholate, leupeptin, pepstatin, soybean trypsin inhibitors, thiorphan, Tos-Lys-chloromethyl ketone, potato carboxypeptidase inhibitor.

Examples of efflux pump inhibitors are, for example, ketoconazole or polyethylene 660 12-hydroxystearate (Solutol® HS 15).

On the basis of scanning electron microscopic images (SEM) of pellets in which the release of active compound in the in-vitro release experiment has just commenced, it can be observed that the three-layer separating layer according to the invention acts really reliably, in that the coating layer at this point in time has already almost always completely separated or dissolved from the core.

The at least two-layer separating layer in particular causes the pharmaceutical forms according to the invention in the form of initially coated pellets, which at the point in time between the 10 and 30% release of active compound are removed from an in-vitro active compound release experiment according to USP, no longer to show clearly discernible remains of the polymer shell to at least 95%, preferably to at least 98%, in scanning electron microscopic images in a random sample of 100 pellets.

On account of remaining residues of the coating, this prevents an uncontrolled premature separation of the active compound from penetration-promoting, mucoadhesive and/or enzyme-inhibiting substance formulated with the active compound and tailored to the active compound occurring. This can even take place if one of the components preferably escapes through partial locally restricted openings of the polymer coating, while the other component still remains behind. According to the invention, it is thus achieved with greater safety that the active compound and the associated penetration-promoting, mucoadhesive and/or enzyme-inhibiting substance simultaneously reach the site of action as intended.

This advantageous action is not restricted to specific active compounds if an assigned substance is present which is intended to promote the administration of the active compound actually contained and in this way to ensure the therapeutic efficacy of the pharmaceutical form. The at least two- or three-layer separating layer also serves to ensure negligible premature and undesired demixing or separation of the active compound and its assigned substance.

In the case of poorly soluble active compounds and in particular in the case of active compounds which are a peptide, a protein, a nucleic acid or a polysaccharide or a derivative of one of the substance classes mentioned, the formulation with penetration-promoting and/or mucoadhesive substances is, however, particularly critical, so the invention can preferably be used for these active compounds. In particular, this aspect of the invention can also be used if the active compound classes mentioned are combined with a substance inhibiting the enzymatic degradation of the active compound, because here the therapeutic effect depends in a particularly critical manner on the fact that the active compound is protected against enzymatic degradation up to its impinging on the site of action.

Gastric Juice-Resistant, Intestinal Juice-Soluble (Meth)Acrylate Copolymers

The pharmaceutical form according to the invention has a coating of a gastric juice-resistant, intestinal juice-soluble (meth)acrylate copolymer. Anionic (meth)acrylate copolymers are suitable.

The anionic (meth)acrylate copolymer can comprise to 25 to 95, preferably to 40 to 95, in particular to 60 to 40, % by weight of free radical-polymerized $C_1$- to $C_4$-alkyl esters of acrylic or of methacrylic acid and to 75 to 5, preferably 60 to 5, in particular 40 to 60, % by weight of (meth)acrylate monomers having an anionic group. The amount of free radical-polymerized $C_1$- to $C_4$-alkyl esters of acrylic or of methacrylic acid includes all values and subvalues therebetween, especially including 30, 35, 40, 45, 50, 55, 60, 65, 70, 75, 80, 85, 90% by weight. The amount of (meth)acrylate monomers having an anionic group includes all values and subvalues therebetween, especially including 70, 65, 60, 55, 50, 45, 40, 35, 30, 25, 20, 15, 10% by weight.

Usually, the proportions mentioned add up to 100% by weight. Additionally, however, without this leading to an impairment or change in the essential properties, small amounts in the range from 0 to 10, e.g. 1 to 5, % by weight of further vinylically copolymerizable monomers, such as, for example, hydroxyethyl methacrylate or hydroxyethyl acrylate can be contained. The amount of vinylically copolymerizable monomers includes all values and subvalues therebetween, especially including 0.5, 1, 2, 4, 6, 8% by weight. Preferably, no further vinylically copolymerizable monomers are contained.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group is, for example, acrylic acid; methacrylic acid is preferred.

Anionic (meth)acrylate copolymers of 40 to 60% by weight of methacrylic acid and 60 to 40% by weight of methyl methacrylate or 60 to 40% by weight of ethyl acrylate (EUDRAGIT® L or EUDRAGIT® L100-55 types) are suitable.

EUDRAGIT® L is a copolymer of 50% by weight of methyl methacrylate and 50% by weight of methacrylic acid. The pH of the beginning of specific release of active compound in intestinal juice or artificial intestinal juice can be indicated as pH 6.0.

EUDRAGIT® L100-55 is a copolymer of 50% by weight of ethyl acrylate and 50% by weight of methacrylic acid. EUDRAGIT® L 30 D-55 is a dispersion comprising 30% by weight of EUDRAGIT® L 100-55. The pH of the beginning of specific release of active compound in intestinal juice or artificial intestinal juice can be indicated as pH 5.5.

Anionic (meth)acrylate copolymers of 20 to 40% by weight of methacrylic acid and 80 to 60% by weight of methyl methacrylate (EUDRAGIT® S type) are likewise suitable. The pH of the beginning of specific release of active compound in intestinal juice or artificial intestinal juice can be indicated as pH 7.0.

(Meth)acrylate copolymers, comprising 10 to 30% by weight of methyl methacrylate, 50 to 70% by weight of methyl acrylate and 5 to 15% by weight of methacrylic acid (EUDRAGIT® FS type) are suitable. The pH of the beginning of specific release of active compound in intestinal juice or artificial intestinal juice can be indicated as pH 7.0.

EUDRAGIT® FS is a copolymer of 25% by weight of methyl methacrylate, 65% by weight of methyl acrylate and 10% by weight of methacrylic acid. EUDRAGIT® FS 30 D is a dispersion comprising 30% by weight of EUDRAGIT® FS.

A copolymer comprising
  20 to 34% by weight of methacrylic acid and/or acrylic acid,
  20 to 69% by weight of methyl acrylate, and
  0 to 40% by weight of ethyl acrylate, and/or optionally
  0 to 10% by weight of further vinylically copolymerizable monomers, is furthermore suitable, with the proviso that the glass transition temperature of the copolymer according to ISO 11357-2, Section 3.3.3 is at most 60° C. Because of its good elongation at break properties, this (meth)acrylate copolymer is suitable in particular for the compression of pellets to give tablets.

Copolymers comprising
  20 to 33% by weight of methacrylic acid and/or acrylic acid,
  5 to 30% by weight of methyl acrylate, and
  20 to 40% by weight of ethyl acrylate, and
  greater than 10 to 30% by weight of butyl methacrylate, and optionally
  0 to 10% by weight of further vinylically copolymerizable monomers,
  where the proportions of the monomers add up to 100% by weight, are furthermore suitable, with the proviso that the glass transition temperature of the copolymer according to ISO 11357-2, Section 3.3.3 (midpoint temperature $T_{mg}$), is 55 to 70° C. Because of their good mechanical properties, copolymers of this type are suitable, in particular, for the compression of pellets to give tablets.

The abovementioned copolymer comprises in particular free radical-polymerized units of
  20 to 33, preferably 25 to 32, particularly preferably 28 to 31, % by weight of methacrylic acid or acrylic acid; methacrylic acid is preferred,
  5 to 30, preferably 10 to 28, particularly preferably 15 to 25, % by weight of methyl acrylate,
  20 to 40, preferably 25 to 35, particularly preferably 18 to 22, % by weight of ethyl acrylate, and
  greater than 10 to 30, preferably 15 to 25, particularly preferably 18 to 22, % by weight of butyl methacrylate,
  where the monomer composition is chosen such that the glass transition temperature of the copolymer is 55 to 70° C., preferably 59 to 66, particularly preferably 60 to 65° C.

Glass transition temperature is understood here in particular as meaning the midpoint temperature $T_{mg}$ according to ISO 11357-2, Section 3.3.3. Measurement is carried out without plasticizer addition, with residual monomer contents (REMO) of less than 100 ppm, at a heating rate of 10° C./min and under a nitrogen atmosphere.

The copolymer consists preferably essentially to exclusively to 90, 95 or 99 to 100% by weight of the monomers methacrylic acid, methyl acrylate, ethyl acrylate and butyl methacrylate in the ranges of amounts indicated above.

Additionally, however, without this having to lead to an impairment of the essential properties, small amounts in the range from 0 to 10, e.g. 1 to 5% by weight of further vinylically copolymerizable monomers, such as, for example, methyl methacrylate, butyl acrylate, hydroxyethyl methacrylate, vinylpyrrolidone, vinylmalonic acid, styrene, vinyl alcohol, vinyl acetate and/or their derivatives can be contained. The amount of vinylically copolymerizable monomers includes all values and subvalues therebetween, especially including 0.5, 1, 2, 4, 6, 8% by weight.

Preparation of the Anionic (Meth)Acrylate Copolymers

The preparation of the anionic (meth)acrylate copolymers can be carried out in a manner known per se by free-radical polymerization of the monomers (see, for example, EP 0 704 207 A2 and EP 0 704 208 A2). The copolymer according to the invention can be prepared in a manner known per se by free-radical emulsion polymerization in aqueous phase in the presence of preferably anionic emulsifiers, for example according to the process described in DE-C 2 135 073.

The copolymer can be prepared continuously or batchwise (batch process) in substance in solution, by bead polymerization or in emulsion according to customary processes of free-radical polymerization in the presence of free radical-forming initiators and optionally regulators for the adjustment of the molecular weight. The average molecular weight Mw (weight average, determined, for example, by measurement of the solution viscosity) can be, for example, in the range from 80 000 to 1 000 000 (g/mol). Emulsion polymerization in aqueous phase in the presence of water-soluble initiators and (preferably anionic) emulsifiers is preferred.

In the case of substance polymerization, the copolymer can be obtained in solid form by breaking, extrusion, granulation or die-face cutting.

The (meth)acrylate copolymers are obtained in a manner known per se by free-radical substance, solution, bead or emulsion polymerization. Before processing, they must be brought to the particle size range according to the invention by suitable grinding, drying or spraying processes. This can be carried out by simple breaking of extruded and cooled granule strands or die-face cutting.

In particular when mixing with further powders or liquids, the use of powders can be advantageous. Suitable implements for the production of the powders are familiar to the person skilled in the art, e.g. air jet mills, pinned disc mills, fan mills. Appropriate sieving steps can optionally be included. A suitable mill for large industrial amounts is, for example, a counter jet mill (Multi No. 4200), which is operated at about 6 bar overpressure.

Partial Neutralization

In a preferred embodiment, the (meth)acrylate copolymer coating of the pharmaceutical form according to the invention is employed in partially neutralized form. The partial neutralization accelerates the dissolution or detachment of the coating layer from the pharmaceutical form. The interaction of dissolution and detachment of the coating layer at the specific pH in a first step and the release of active compound immediately following only then is thus favoured.

The anionic (meth)acrylate copolymer of the coating can be entirely or proportionately partially neutralized in total by means of a base. If a mixture is not present, the (meth)acrylate copolymer present is uniformly partially neutralized. In the case of mixtures, unneutralized (meth)acrylate copolymer can be present in a mixture with completely and/or partially neutralized (meth)acrylate copolymer. Optionally, mixtures of (meth)acrylate copolymers of different degrees of neutralization or partial neutralization can also be present.

The anionic groups of the (meth)acrylate copolymer entirely present should here preferentially be neutralized in total, i.e. optionally in the arithmetic mean, to 0.1 to 25, particularly preferably to 5 to 15, %.

It is known to employ anionic (meth)acrylate copolymers in partially neutralized form. An improved solubility of the polymer in water and a stabilization of the polymer dispersions is thus achieved. Bases specified for the partial neutralization are usually substances such as NaOH, KOH, ammonium hydroxide or organic bases, such as, for example, triethanolamine (see, for example, EP 0 088 951 A2 or WO 2004/096185).

If films of anionic (meth)acrylate copolymer partially neutralized and not partially neutralized by means of NaOH are compared, for example, it is observed that the partially neutralized films dissolve more rapidly in a buffer system at their specific dissolution pH than the not neutralized films.

The following effect was previously unknown: The inventors have observed that the behaviour of partially neutralized films described above and of partially neutralized films of coated pharmaceutical forms only shows up to a decreased extent if bases which are known from EP 0 088 951 A2 or WO 2004/096185 (e.g. NaOH) are employed for the partial neutralization if the films or pharmaceutical forms are first left at pH 1.2 for 2 hours before rebuffering them to the specific pH of the beginning of the release of active compound. Precisely these conditions, however, are present in vivo, when a pharmaceutical form first reaches the stomach and is then only transported to the intestinal tract. The partial neutralization of anionic (meth)acrylate copolymers mentioned above is therefore only suitable to a limited extent for producing an accelerated active compound release behaviour.

An improved acceleration effect in vivo can be achieved if lysine ($M_w$ 146) or a cationic, organic base having an $M_w$>150, preferably >155, particularly preferably >160, e.g. of >150 to 20 000, is employed for the partial neutralization: lysine or the cationic, basic amino acids histidine, arginine are suitable in particular. The amino acids glutamine and asparagine are barely suitable or not suitable, since they do not have a non-protonated acid amide function and are thus not to be counted amongst the cationic bases.

Natural or synthetic oligomers or polymers, e.g. of 3 to 100, preferably 5 to 25, units, of histidine, arginine or lysine, polyhistidines, polyarginines, polylysines, cationic or zwitterionic phospholipids, such as, for example, phosphatidylcholine, can furthermore be suitable for the partial neutralization.

Ribonucleosides can furthermore be suitable for the partial neutralization: condensation products of the hydroxyl function on carbon atom 1 of ribose with the heterocyclic amino function of the bases adenine, guanine, cytosine, thymine or uracil, corresponding to occurrence in the RNA.

Deoxyribonucleosides can furthermore be suitable for the partial neutralization: condensation products of the hydroxyl function on carbon atom 1 of the deoxyribose with the heterocyclic amino function of the bases adenine, guanine, cytosine, thymine or uracil, corresponding to occurrence in the DNA.

Bases of cationic surface-active excipients or emulsifiers, such as benzalkonium (CAS RN: 8001-54-5), benzethonium (CAS 121-54-0), cetalkonium (CAS 122-18-9), cetrimide (CAS 8044-71-1), cetrimonium (CAS 57-09-0), cetylpyridinium (CAS 123-03-5), stearalkonium (CAS 122-19-0), diallyldimethylammonium (CAS 230-993-8) can furthermore be suitable for the partial neutralization.

Bases which are mentioned in EP 0 088 951 A2 or WO 2004/096185 are suitable to a limited extent for the purposes of the invention. In particular: sodium hydroxide solution, potassium hydroxide solution (KOH), ammonium hydroxide or organic bases such as, for example, triethanolamine, soda, potash, sodium bicarbonate, trisodium phosphate, trisodium citrate or ammonia or physiologically tolerable amines, such as triethanolamine or tris(hydroxymethyl)aminomethane.

These bases have an Mw of at most 150 (triethanolamine). Although triethanolamine is close with its molecular weight to the amino acids histidine, arginine, lysine, the dissolution-accelerating effect of this substance in vivo only takes place to a small extent. Trisodium phosphate, trisodium citrate are not of cationic nature, but salts of the corresponding acids. Ammonium hydroxide, sodium hydroxide solution, potassium hydroxide solution (KOH), soda, potash, sodium bicarbonate only have low molecular weights or are to be counted amongst the inorganic bases.

Preferably, the polymer coating contains lysine or arginine or arginine and lysine as partial neutralizing agents.

Particularly preferably, the polymer coating contains lysine in a concentration of 10 to 30% by weight, based on the dry substance of the polymer.

In particular, the polymer coating can contain lysine or arginine or arginine and lysine as neutralizing agents in combination with 5 to 25, preferably 8 to 20, % by weight of a plasticizer based on the polymer. The amount of plasticizer includes all values and subvalues therebetween, especially including 6, 8, 10, 12, 14, 16, 18, 20, 22 and 24% by weight.

The molecular weight of the substances mentioned is known or can be calculated on the basis of the atoms present in the molecule on the basis of the atomic weights.

Adjustment of the Degree of Partial Neutralization by Mixtures

Process technology advantages in the adjustment of the degree of partial neutralization can also result by means of the mixtures already mentioned above.

It is possible, for example, to mix a not partially neutralized, anionic (meth)acrylate copolymer, consisting of free radical-polymerized units of 25 to 95% by weight of $C_1$- to $C_4$-alkyl esters of acrylic or of methacrylic acid and 5 to 75% by weight of (meth)acrylate monomers having an anionic group with a partially neutralized (meth)acrylate copolymer of identical monomer composition, such that preferentially 0.1 to 25% of the anionic groups contained in the arithmetic average of the mixture are neutralized. The amount of free radical-polymerized units of $C_1$- to $C_4$-alkyl esters of acrylic or of methacrylic acid includes all values and subvalues therebetween, especially including 30, 35, 40, 45, 50, 55, 60, 65, 70, 75, 80, 85 and 90% by weight. The amount of free radical-polymerized units of (meth)acrylate monomers having an anionic group includes all values and subvalues therebetween, especially including 10, 15, 20, 25, 30, 35, 40, 45, 50, 55, 60, 65, 70% by weight.

The mixture can be prepared, for example, by stirring a powder which has been obtained from a dispersion of a partially neutralized, anionic (meth)acrylate copolymer, e.g. by spray- or freeze-drying, into a dispersion of a not partially neutralized, anionic (meth)acrylate copolymer.

Mixtures

The gastric juice-resistant, intestinal juice-soluble and optionally partially neutralized (meth)acrylate copolymer covering the core is usually employed without admixture of further polymers. The (meth)acrylate copolymer is also suitable, however, for mixture with other pharmaceutically utilized copolymers in order to modify the properties. Mixtures increase the design freedom of the person skilled in the art in the adjustment of specially modified release profiles.

Mixtures of the gastric juice-resistant, intestinal juice-soluble and optionally partially neutralized (meth)acrylate copolymer covering the core can therefore be present with:

copolymers of methyl methacrylate and/or ethyl acrylate and optionally less than 5% by weight of methacrylic acid, with copolymers of methyl methacrylate, butyl methacrylate and dimethylethyl methacrylate, with copolymers of methyl methacrylate, ethyl acrylate and trimethylammoniumethyl methacrylate, polyvinylpyrolidones (PVP), polyvinyl alcohols, polyvinyl alcohol-polyethylene glycol graft copolymers (Kollicoat®), starch and its derivatives, polyvinyl acetate phthalate (PVAP, Coateric®), polyvinyl acetate (PVAc, Kollicoat), vinyl acetate-vinylpyrrolidone copolymer (Kollidon® VA64), vinyl acetate:crotonic acid copolymer 9:1 (VAC: CRA, Kollicoat® VAC), polyethylene glycols having a molecular weight of over 1000 (g/mol), chitosan, a crosslinked and/or uncrosslinked polyacrylic acid, an Na alginate, and/or a pectin.

Preferably, the proportion of the gastric juice-resistant, intestinal juice-soluble (meth)acrylate copolymer in the mixture is at least 50% by weight, particularly preferably at least 75% by weight, in particular at least 90 or preferably at least 95, % by weight, such that its properties dominate.

Dispersions

The optionally partially neutralized (meth)acrylate copolymer can be present, for example, in the form of an aqueous dispersion having a 10 to 50 percent solids content.

The optionally partially neutralized (meth)acrylate copolymer can be present in the form of a redispersable powder, which has been obtained from a dispersion, for example, by spray-drying.

Dispersions/Partial Neutralization

The emulsion polymer is preferably prepared and used in the form of a 10 to 50 percent by weight, in particular 20 to 40 percent by weight, aqueous dispersion. As a commercial form, a solids content of about 30% by weight is preferred. For processing, a partial neutralization of the methacrylic acid units is indispensable; it is possible, however, for example in an extent of up to 5 or 10 mol %, if a stabilization or thickening of the coating agent dispersion should be desired. The weight average value latex particle size (radius) is usually 40 to 100 nm, preferably 50 to 70 nm, which guarantees a viscosity of below 1000 mPa·s, which is favourable in processing technology terms. The weight average value latex particle size includes all values and subvalues therebetween, especially including 45, 50, 55, 60, 65, 70, 75, 80, 85, 90 and 95 nm. The particle size can be determined by laser diffraction, e.g. using the Mastersizer 2000 (Malvern).

In the case of higher degrees of neutralization, e.g. 10 to 50 mol % or complete neutralization, it is possible to convert the copolymer to a dissolved state.

In order to prepare a solution of the anionic copolymer, usually a partial or complete neutralization of the acid groups is necessary. The anionic copolymer can be stirred in, for example, gradually in a final concentration of 1 to 40% by weight in water and in the course of this can be partially or completely neutralized by addition of a basic substance such as, for example, lysine or arginine. It is also possible to employ a powder of the copolymer, to which a base, for example lysine, has already been added in its preparation for the purpose of (partial) neutralization, such that the powder is an already (partially) neutralized polymer. The pH of the solution is usually over 4, e.g. in the range from 4 to about 7. It is also possible here to make, for example, mixtures of batches of completely or partially neutralized dispersions with not neutralized dispersions and to further process them in the manner described, i.e. use the mixture for coatings or first freeze- or spray-dry to give a powder.

The dispersion can, for example, also be spray-dried or freeze-dried in a manner known per se and prepared in the form of a redispersable powder (see, for example, EP-A 0 262 326). Alternative processes are freeze-drying or coagulation and squeezing off of the water in an extruder with subsequent granulation (see, for example, EP-A 0 683 028).

Copolymer dispersions of spray- or freeze-dried and redispersed powders can have an increased shear stability. This is advantageous in particular on spray application. This advantage in particular occurs to an increased extent if the copolymer contained in the dispersion is present to 2 to 10, preferably to 5 to 7, mol % in partially neutralized form (based on the acid groups contained in the copolymer). Partial neutralization by means of addition of lysine or arginine is preferred for this purpose. Preferably, an anionic emulsifier is contained in an amount of 0.1 to 2% by weight. Sodium lauryl sulphate is particularly preferred as the emulsifier.

Use of the Partially Neutralized (Meth)Acrylate Copolymer

The anionic (meth)acrylate copolymers partially neutralized with a cationic, organic base having an $M_w>150$ or with lysine can preferably be used as coating agents for the pharmaceutical form according to the invention. Here, approximately 90%, preferably 95 or 100% of the contained active compound in the release test according to USP 28 for 2 hours at pH 1.2 and subsequent rebuffering to the pH of the beginning of the release of active compound is free after rebuffering in at most 90%, preferably at most 75%, in particular at most 50% of the time which elapses for this in a comparable pharmaceutical form having an identical polymer coat, but without neutralization or partial neutralization by means of other bases.

If a partially neutralized pharmaceutical form not neutralized with lysine or with a cationic, organic base having an $M_w>150$ releases the active compound in the release test according to USP 28 for 2 hours at pH 1.2 and subsequent rebuffering to the pH of the beginning of the release of active compound, e.g. pH 5.5, in, for example, 120 min after rebuffering to 90%, a comparable pharmaceutical form whose coating has been partially neutralized by means of lysine or a cationic, organic base having an $M_w>150$, needs at most 108 min (90% of the time), at most 90 min (75%) or at most 60 min (50%).

The release test specified according to USP 28, in particular according to USP 28 <711> paddle method (=Apparatus 2), is adequately known to the person skilled in the art The typical test procedure is as follows:
1. The vessels of the release apparatus are filled with 360 ml each of 0.1M HCl (pH 1.2) and the temperature of the water bath is adjusted to 37±0.5° C.
2. The blade stirrer is switched on with a rate of rotation of 100 rpm.
3. 1 g of pellets is added to each vessel of the apparatus. Care is to be taken that there are no air bubbles on the pellet surface.
4. After 120 min, 140 ml of phosphate buffer solution (warmed to 37° C.) are added, such that the desired pH results in the final volume of 500 ml: pH 5.5; 5.6; 5.7; 5.8 or 7.0.
5. Determination of the time of 100% release of active compound, depending on active compound, e.g. in the case of theophylline photometrically at 271 nm, in the recirculation procedure.

Pharmaceutical Form

The invention relates to a pharmaceutical form, comprising an active compound-containing core, which is covered with a coating layer of a gastric juice-resistant, intestinal juice-soluble (meth)acrylate copolymer, where between the core and the coating layer is situated a separating layer, comprising a film-forming water-soluble polymer, characterized in that the separating layer is designed to be at least two-layer, an inner layer containing a water-repellent substance and thereon a layer containing the film-forming water-soluble polymer being present.

Preferably, the separating layer is designed to be three-layer, two layers of the film-forming water-soluble polymer enclosing a layer containing the water-repellent substance.

The pharmaceutical form can preferably contain a polymer coating with lysine or arginine as the partial neutralizing agent in combination with 5 to 25% by weight of a plasticizer, based on the polymer.

The pharmaceutical form according to the invention can be present, for example, in the form of a multiparticulate pharmaceutical form, pellet-containing tablets, minitablets, capsules, sachets, effervescent tablets or inspissated juices.

Process for the Production of a Pharmaceutical Form

The invention furthermore relates to a process for the production of the pharmaceutical form according to the invention in a manner known per se by means of pharmaceutically customary processes, such as direct compression, compression of dry, moist or sintered granules, extrusion and subsequent rounding, moist or dry granulation or direct pelleting or by binding of powders (powder layering), by spraying suspensions or solutions onto active compound-free beads or neutral cores (nonpareils) or active compound-containing particles and by means of application of the polymer coating in the spray process or by fluidized bed granulation.

Production of Multiparticulate Pharmaceutical Forms

The invention is suitable in particular for the production of multiparticulate pharmaceutical forms, since the covering (meth)acrylate copolymer withstands the high pressures in the compression of the pellets with the filler.

The production of multiparticulate pharmaceutical forms by compression of a pharmaceutically customary binder with active compound-containing particles is described in detail, for example, by Beckert et al. (1996), "Compression of enteric-coated pellets to disintegrating tablets", *International Journal of Pharmaceutics* 143, pp. 13-23, and in WO 96/01624.

Active compound-containing pellets can be produced by applying active compound by means of a layering process. To this end, active compound is homogenized together with further excipients (release agents, optionally plasticizers) and dissolved or suspended in a binder. By means of a fluidized bed process, the liquid can be applied to placebo pellets or other suitable carrier materials, the solvent or suspending agent being evaporated (Literature: *International Journal of Pharmaceutics* 143, pp. 13-23). After the production process, a drying step can follow. The active compound can be applied in a number of layers.

Some active compounds, e.g. acetylsalicylic acid, are commercially available in the form of active compound crystals and can be employed in this form instead of active compound-containing pellets.

Film coatings on active compound-containing pellets are customarily applied in fluidized bed apparatuses. Formulation examples are mentioned in this application. Film-forming agents are customarily mixed with plasticizers and release agents according to a suitable process. Here, the film-forming agents can be present as a solution or suspension. The excipients for the film formation can likewise be dissolved or suspended. Organic or aqueous solvents or dispersants can be used. For the stabilization of the dispersion, stabilizers can additionally be used (Example: Tween 80 or other suitable emulsifiers or stabilizers).

Examples of release agents are glycerol monostearate or other suitable fatty acid derivatives, silicic acid derivatives or talc. Examples of plasticizers are propylene glycol, phthalates, polyethylene glycols, sebacates or citrates, and other substances mentioned in the literature.

A separating layer can be applied between active compound-containing and intestine-soluble copolymer layer, which serves for the separation of active compound and coating material for the purpose of the prevention of interactions. This layer can consist of inert film-forming agents (e.g. HPMC, HPC or (meth)acrylic acid copolymer) or, for example, talc or other suitable pharmaceutical substances. Likewise, combinations of film-forming agents and talc or similar substances can be used.

It is also possible to apply a separating layer of partially or completely neutralized copolymer dispersions.

Mixtures for the production of tablets from coated particles are prepared by mixing the pellets with suitable binders for tabletting, if necessary the addition of disintegration-promoting substances and if necessary the addition of lubricants. Mixing can take place in suitable machines. Mixers which lead to damage to the coated particles are unsuitable, e.g. ploughshare mixers. For achieving suitable short disintegration times, a special sequence may be necessary in the addition of the excipients to the coated particles. By premixing of the coated particle with the lubricant or mould-release agent magnesium stearate, its surface can be hydrophobized and thus sticking can be avoided.

Mixtures suitable for tabletting customarily contain 3 to 15% by weight of a disintegrant, e.g. Kollidon CL, and, for example, 0.1 to 1% by weight of a lubricant and mould-release agent such as magnesium stearate. The proportion of binder is determined according to the required proportion of coated particles.

Typical binders are, for example, Cellactose®, microcrystalline cellulose, calcium phosphates, Ludipress®, lactose or other suitable sugars, calcium sulphates or starch derivatives. Substances having a low bulk density are preferred.

Typical disintegrants are crosslinked starch or cellulose derivatives, and crosslinked polyvinylpyrrolidone. Cellulose derivatives are likewise suitable. By selection of a suitable binder, the use of disintegrants can be dispensed with.

Typical lubricants and mould-release agents are magnesium stearates or other suitable salts of fatty acids or substances mentioned in the literature for this purpose (e.g. lauric acid, calcium stearate, talc etc.). When using suitable machines (e.g. a tablet press with external lubrication) or suitable formulations, the use of a lubricant and mould-release agent in the mixture can be dispensed with.

An excipient for flow improvement can optionally be added to the mixture (e.g. highly disperse silicic acid derivatives, talc etc.).

Tabletting can be carried out in customary tablet presses, eccentric presses or rotary tablet presses, at compressive forces in the range from 5 to 40 kN, preferably 10-20 kN. The tablet presses can be provided with systems for external lubrication. Optionally, special systems for matrix filling are used, which avoid matrix filling by means of stirrer blades.

Further Production Processes for the Pharmaceutical Form According to the Invention The application process takes place by means of spray application from organic solution, or preferably aqueous dispersions by melting or by direct powder application. For implementation, it is crucial here that uniform, pore-free coatings result.

For application conventional processes according to, for example, Bauer, Lehmann, Osterwald, Rothgang, "Uberzogene Arzneiformen" [Coated Pharmaceutical Forms] Wissenschaftliche Verlagsgesellschaft mbH Stuttgart, Chap. 7, pp. 165-196, may be used.

For application, relevant properties, required tests and specifications are listed in pharmacopoeias.

Details can be taken from the customary textbooks, e.g.:
Voigt, R. (1984): Lehrbuch der pharmazeutischen Technologie [Textbook of Pharmaceutical Technology]; Verlag Chemie Weinheim-Beerfield Beach/Florida-Basle.
Sucker, H., Fuchs, P., Speiser, P.: Pharmazeutische Technologie [Pharmaceutical Technology], Georg Thieme Verlag Stuttgart (1991), in particular Chapters 15 and 16, pp. 626-642.
Gennaro, A., R. (Editor), Remington's Pharmaceutical Sciences, Mack Publishing Co., Easton Pa. (1985), Chapter 88, pp. 1567-1573.
List, P. H. (1982): Arzneiformenlehre [Pharmaceutical Form Theory], Wissenschaftliche Verlagsgesellschaft mbH, Stuttgart.

Excipients

Customary excipients and/or additives can be added to the formulations according to the invention during production. In principle, all substances employed must of course be toxicologically harmless and in particular able to be used in medicaments without risk for patients.

Amounts used and use of the customary additives in pharmaceutical coatings or coatings are familiar to the person skilled in the art. Customary additives can be, for example, plasticizers, release agents, pigments, stabilizers, antioxidants, pore-forming agents, penetration promoters, lustre agents, flavourings, detergents, lubricants or flavouring agents. They serve as processing aids and should guarantee a safe and reproducible production process and good long-term storage stability or they achieve additional advantageous properties in the pharmaceutical form. They are added to the polymer preparations before processing and can influence the permeability of the coatings, which optionally can be utilized as an additional control parameter.

Release Agents:

Release agents usually have lipophilic properties and are usually added to the spray suspensions. They prevent an agglomeration of the cores during film-coating. Preferably, talc, Mg or Ca stearate, ground silicic acid, kaolin or nonionic emulsifiers having an HLB between 3 and 8 are employed. Customary amounts used for release agents in the coating agents and binders according to the invention are between 0.5 and 100% by weight based on the copolymer.

Pigments:

Pigments incompatible with the coating agents are in particular those pigments which, if they are directly added to the (meth)acrylate copolymer dispersion, e.g. by stirring in, in customary application amounts of, for example, 20 to 400% by weight based on the dry weight of the (meth)acrylate copolymer, can lead to the destabilization of the dispersion, coagulation, to demixing phenomena or similarly undesired effects. Furthermore, the pigments to be used are of course non-toxic and suitable for pharmaceutical purposes. For this see also, for example: Deutsche Forschungsgemeinschaft, *Farbstoffe für Lebensmittel* [German Research Association, *Colorants for Foodstuffs*], Harald Boldt Verlag K G, Boppard (1978); Deutsche Lebensmittelrundschau 74, No. 4, p. 156

(1978); Arzneimittelfarbstoffverordnung [Medicaments Colorant Directive] AmFarbV of Aug. 25, 1980.

Pigments incompatible with the coating composition can be, for example, aluminium oxide pigments. Incompatible pigments are, for example, Yellow Orange, Cochineal red lake, color pigments based on aluminium oxide or azo dyes, sulphonic acid dyes, Yellow Orange S (E1 10, C.I. 15985, FD&C Yellow 6), Indigo Carmine (E132, C.I. 73015, FD&C Blue 2), Tartrazine (E 102, C.I. 19140, FD&C Yellow 5), Ponceau 4R (E 125, C.I. 16255, FD&C Cochineal Red A), Quinoline Yellow (E 104, C.I. 47005, FD&C Yellow 10), Erythrosine (E127, C.I. 45430, FD&C Red 3), Azorubine (E 122, C.I. 14720, FD&C Carmoisine), Amaranth (E 123, C.I. 16185, FD&C Red 2), Brilliant Acid Green (E 142, C.I. 44090, FD&C Green S).

The indicated E numbers of the pigments refer to EU numbering. For this, also see "Deutsche Forschungsgemeinschaft, Farbstoffe fur Lebensmittel", Harald Boldt Verlag K G, Boppard (1978); Deutsche Lebensmittelrundschau 74, No. 4, pp. 156 (1978); Arzneimittelfarbstoffverordnung AmFarbV of Aug. 25, 1980. The FD&C numbering refer to the licence in Food, Drugs and Cosmetics by the U.S. Food and Drug Administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Plasticizers

Further additives can also be plasticizers. Customary amounts are between 0 and 50, preferably 2 to 20, in particular 5 to 10, % by weight.

Depending on type (lipophilic or hydrophilic) and amount added, plasticizers can influence the functionality of the polymer layer. By means of physical interaction with the polymer, plasticizers achieve a lowering of the glass transition temperature and, depending on the amount added, promote film formation. Suitable substances usually have a molecular weight of between 100 and 20 000 and contain one or more hydrophilic groups in the molecule, e.g. hydroxyl, ester or amino groups.

Examples of suitable plasticizers are citric acid alkyl esters, glycerine esters, phthalic acid alkyl esters, sebacic acid alkyl esters, sucrose esters, sorbitan esters, diethyl sebacate, dibutyl sebacate and polyethylene glycols 200 to 12 000. Preferred plasticizers are triethyl citrate (TEC) and acetyltriethyl citrate (ATEC). Mention may furthermore be made of esters which are usually liquid at room temperature, such as citrates, phthalates, sebacates or castor oil. Citric acid esters and sebacic acid esters are preferably used.

The addition of the plasticizers to the formulation can be performed in a known manner, directly, in aqueous solution or after heat pretreatment of the mixture. Mixtures of plasticizers can also be employed.

Emulsifiers

Emulsifiers are usually employed in order to improve the sprayability and the flexibility of the resulting layers or films. The use of emulsifiers can take place, for example, in a concentration of 0.1 to 50% by weight based on the total weight of the layer or of the film concerned. The amount of emulsifier includes all values and subvalues therebetween, especially including 0.5, 1, 5, 10, 15, 20, 25, 30, 35, 40 and 45% by weight based on the total weight of the layer or of the film concerned.

For layers of water-soluble polymers, such as, for example, the layer(s) of the separating layer containing the film-forming water-soluble polymer, emulsifiers having an HLB according to Griffin of greater than 8 can be employed. Those preferred are, for example, sodium dodecylsulphate, polysorbate (Tween® 20 to 80), polyoxyethylene-polyoxypropylene block polymers (Poloxamer®, Pluronic®), polyethylene glycol-fatty alcohol ethers (Cremophor®), polyoxyethylene fatty alcohol ethers (Brij®), sucrose fatty acid esters (Crodesta®), polyoxyethylene-stearyl alcohols (Emulgin®, Cetomacrogol®).

For layers of water-repellent substances, such as, for example, the layer of the separating layer containing the water-repellent substance, emulsifiers having an HLB according to Griffin of 8 or less than 8 can be employed. By this means, in particular the micellar dissolution of the water-repellent layer can again be accelerated. The addition of emulsifier can thus be used as a further control element.

Examples of emulsifiers having HLBs of 8 or less than 8 are: wool wax alcohols (Agnowax®, Hartolan®, Eucerit®), glycerine esters of fatty acids, such as, for example, glyceryl monooleate, glyceryl monococoate or glyceryl monolaurate, sorbitan esters, such as, for example, sorbitan trioleate (Span® 85), sorbitan monostearate, (Span® 60. Arlacel® 80), sorbitan monopalmitate (Grill® 1, Arlacel®20, Span® 20), sucrose esters, such as, for example, sucrose tristearate, sucrose distearate, sucrose dipalmitate, PEG (200) monostearate or hydrogenated castor oil.

The HLB is a measure of hydrophilicity or lipophilicity of non-ionic surfactants introduced by Griffin in 1950. It can be determined experimentally by the phenol titration method according to Marszall; cf. "Parfimerie, Kosmetik" [Perfumery, Cosmetics], Volume 60, 1979, pp. 444-448; further references in Rompp, Chemie-Lexikon [Chemical Encyclopaedia], 8th ed. 1983, pp. 1750. See furthermore, for example, U.S. Pat. No. 4,795,643 (Seth)).

An HLB (hydrophilic/lipophilic balance) can only be determined exactly in the case of non-ionic emulsifiers. In the case of anionic emulsifiers this value can be determined arithmetically, but is virtually always above or far above 14.

Active Compounds/Pharmaceutical Substances

Customary pharmaceutical substances can be taken from reference works, such as, for example, the Rote Liste or the Merck Index.

The pharmaceutical substances employed within the meaning of the invention are intended to be used on the or in the human or animal body in order 1. to cure, to relieve, to prevent or to diagnose illnesses, complaints, bodily defects or pathological symptoms.
2. to be able to diagnose the state, the condition or the functions of the body or mental conditions.
3. to replace active compounds or body fluids produced by the human or animal body.
4. to protect against, to eliminate or to render harmless pathogens, parasites or exogenous substances, or
5. to influence the state, the condition or the functions of the body or mental conditions.

Therapeutic Classes

These pharmaceutically active substances can belong to one or more classes of active compound, such as ACE inhibitors, adrenergics, adrenocorticosteroids, acne therapeutics, aldose reductase inhibitors, aldosterone antagonists, alpha-glucosidase inhibitors, alpha 1-antagonists, agents against alcohol abuse, amino acids, amoebicides, anabolics, analeptics, anaesthetic additives, anaesthetics (non-inhalative), anaesthetics (local), analgesics, androgens, angina therapeutics, antagonists, antiallergics, anti-allergics such as PDE inhibitors, antiallergics for asthma treatment, further antiallergics (e.g. leukotriene antagonists), antianaemics, antiandrogens, antianxiolytics, antiarthritics, antiarrhythmics, antiatherosclerotics, antibiotics, anti-holinergics, anticonvulsives, antidepressants, antidiabetics, antidiarrhoeals, antidiuretics, antidotes, antiemetics, antiepileptics, antifibrinolytics, anthelmintics, antihistaminics, antihypotensives, anti hypertensives, antihypertonics, antihypotonics, anticoagulants, antimycotics, antioestrogens, antioestrogens (non-steroidal), antiparkinson agents, antiinflammatories, antiproliferative active compounds, antiprotozoal active compounds, anti-rheumatics, antischistosomicides, antispasmolytics, antithrombotics, antitussives, appetite suppressants, arteriosclerotic agents, bacteriostatics, beta-receptor blockers, bronchodilators, carboanhydrase inhibitors, chemotherapeutics, choleretics, cholinergics, cholinesterase inhibitors, agents for the treatment of ulcerative colitis, cyclooxygenase inhibitors, diuretics, ectoparasiticides, emetics, enzymes, enzyme inhibitors, fibrinolytics, fungistatics, gout agents, glaucoma therapeutics, glucocorticoids, glucocorticosteroids, haemostatics, cardiac glycosides, histamine H2 antagonists, hormones and their inhibitors, immunotherapeutics, cardiotonics, coccidiostatics, laxatives, lipid-lowering agents, gastrointestinal therapeutics, malaria therapeutics, migraine agents, microbicides, agents for the treatment of Crohn's disease, metastasis inhibitors, mineral preparations, motility-increasing active compounds, muscle relaxants, neuroleptics, active compounds for the treatment of osteoporosis, otologics, parkinson agents, phytopharmaceuticals, proton pump inhibitors, prostaglandins, active compounds for the treatment of benign prostate hyperplasia, active compounds for the treatment of pruritus, psoriasis active compounds, psychopharmaceuticals, free-radical scavengers, renin antagonists, thyroid therapeutics, active compounds for the treatment of seborrhoea, spasmolytics, alpha- and beta-sympathomimetics, platelet aggregation inhibitors, tyrosine kinase inhibitors, tranquillizers, ulcer therapeutics, agents for the treatment of urolithiasis, virustatics, vitamins, cytokines, cytostatics.

Active Compounds

Examples of suitable active compounds are acarbose, acetylsalicylic acid, abacavir, aceclofenac, aclarubicin, acyclovir, actinomycin, adalimumab, adefovir, adefovir dipivoxil, adenosylmethionine, adrenaline and adrenaline derivatives, agalsidase alpha, agalsidase beta, alemtuzumab, alfuzosine, allopurinol, almotriptan, alosetrone, alphacept, alprazolam, alprostadil, amantadine, ambroxole, amisulpride, amlodipine, amoxicillin, 5-aminosalicylic acid, amitriptyline, amprenavir, anagrelide, anakinra, anastrozole, androgen and androgen derivatives, apomorphine, aripiprazole, arsenic trioxide, artemether, atenolol, atorvastatin, atosiban, azathioprine, azelaic acid, barbituric acid derivatives, balsalazide, basiliximab, beclapermin, beclomethasone, bemiparin, benazepril, benzodiazepines, beraprost, betahistine, bexarotene, bezafibrate, bicalutamide, bimatoprost, bismuth citrate, bismuth subsalicylate, bosentan, botulinum toxim, brimonidine, brinzolamide, bromacepam, bromocriptine, budesonide, budipine, bufexamac, bumetamide, buprenorphine, bupropion, butizine, calcitonin, calcium antagonists, calcium carbonate, calcium dobesilate, calcium salts, camazepam, candesartan, capecitabin, captopril, carbamazepine, carifenacin, carvedilol, caspofungin, cefaclor, cefadroxil, cefalexin cephalosporins, cefditorene, cefprozil, cefuroxime, celecoxib, cepecitabine, cerivastatim, cetirizine, cetrorelix, cetuximab, chenodeoxycholic acid, chlordiazepoxide, choriogonadotropin, ciclosporin, cidofovir, cilazapril, cimetidine, ciprofloxacin, cisplatin, cladribine, clarithromycin, clavulanic acid, clindamycin, clobazam, clobutinol, clonazepam, clonidine, clopidogrel, codeine, caffeine, colestyramine, cromoglicic acid, cotrimoxazole, coumarin and coumarin derivatives, cysteamine, cysteine, cytarabine, cyclophosphamide, cyproterone, cytarabine, daclizumab, dalfopristine, danaparoid, dapiprazole, darbepoetin, defepriprone, desferroxamine, desipramine, desirudine, desloaratadine, desmopressin, desogestrel, desonide, dexibuprofen, dexketoprofen, didanosine, disoproxil, diazepam and diazepam derivatives, didanosine, dihydralazine, diltiazem, dimenhydrinate, dimethyl sulphoxide, dimeticone, dipivoxil, dipyridamol, dolasetrone, domperidone and domperidan derivatives, donepzil, dopamine, doxazosine, doxorubicin, doxylamine, diclofenac, divalproex, dronabinol, drospirenone, drotrecogin alpha, duloxetin, dutasteride, ebastine, econazole, efavirenz, eletripan, emidastine, emtricitabin, enalapril, encepur, entacapon, enfurvirtid, ephedrine, epinephrine, eplerenone, epoetin and epoetin derivatives, eprosartan, eptifibatide, ertapenem, esomeprazole, oestrogen and oestrogen derivatives, etanercept, ethenzamide, ethinoestradiol, etofenamate, etofibrate, etofylline, etonorgestrel, etoposide, etoricoxib, exemestan, ezetimib, famciclovir, famotidine, faropenandaloxat, felodipine, fenofibrate, fenofibric acid, fenoldopam, fentanyl, fenticonazole, fexofenadine, finasteride, fluconazole, fludarabine, flunarizine, fluorouracil, fluoxetine, flurazepam, flurbiprofen, flupirtine, flutamide, fluvastatin, follitropin, fomivirsen, fondaparinux, formoterol, fosfomicin, fosinopril, frovatriptan, furosemide, fusidic acid, gabapentine, gadobenate, galantamine, gallopamil, ganciclovir, ganirelix, gatifloxacin, gefitinib, gemfibrozil, gemopatrilate, gentamicin, gepirone, gestagen and gestagen derivatives, ginkgo, glatiramer, glibenclamide, glimeprides, glipizides, glucagon, glucitol and glucitol derivatives, glucosamine and glucosamine derivatives, glycoside antibiotics, glutathione, glycerol and glycerol derivatives, hypothalamus hormones, goserelin, granisetrone, grepafloxacin, guanethidin, gyrase inhibitors, haemin, halofantrin, haloperidol, urea derivatives as oral antidiabetics, heparin and heparin derivatives, cardiac glycosides, hyaluronic acid, hydralazine, hydrochloro-thiazide and hydrochlorothiazide derivatives, hydroxyomeprazole, hydroxyzine, ibritumomab, ibuprofen, idarubicin, ifliximab, ifosfamide, iloprost, imatinib, imidapril, imiglucerase, imipramine, imiquimod, imidapril, indometacin, indoramine, infliximab, insulin, insulin glargin, interferons, irbesartan, irinotecan, isoconazole, isoprenaline, isorbide mononitrate, isorbide dinitrate, itraconazole, ivabradines, iodine and iodine derivatives, St John's wort, potassium salts, ketoconazole, ketoprofen, ketotifen, lacidipine, lamivudine, lamotrigine, lansoprazole, laronidase, latanoprost, leflunomide, leminoprazole, lepirudine, lercanidipine, leteprinime, letrozole, levacetylmethadol, levetiracetam, levocetirizine, levodopa, levodropropizine, levofloxacin, levomethadone, licofelone, linezolide, lipinavir, lipoic acid and lipoic acid derivatives, lisinopril, lisuride, lofepramine, lodoxamide, lomefloxacin, lomustine, loperamide, lopinavir, loratadine, lomoxicam, losartan, lovastatin, lumefantrin, lutropine, magnesium salts, macrolide antibiotics, mangafodipir, maprotilin, mebendazole, mebeverine, meclozine, mefenamic acid, mefloquine, meloxicam, memantin, mepindolol, meprobamate, meropenem, mesalazine, mesoprostol, mesuximide, metamizole, metaxalone, metformin, methadone, methotrexate, methyl5-amino-4-oxopentanoate, methylnaloxone, methylnaltrexone, methyl phenidate, methylprednisolone, metixene, metoclopramide, metoprolol, metronidazole, mianserine, mibefradil, miconazole, mifepristone, miglitol, miglustad, milnacipran, minocycline, minoxidil, misoprostol, mitomycin, mizolastine, modafinil, moexipril, molsidomine, montelukast, moroctocog, morphinans, morphine and morphine derivatives, moxifloxacin, ergot alkaloids, nalbuphine, naloxone, naproxen, naratriptan, narcotine, natamycin, nateglinide, nebivolol, nefazodone, nelfinavir, neostigmine, neramexan, nevirapine, nicergoline, nicethamide, nifedipine, niflumic acid, nilutamide, nimodipine, nimorazole, nimustine, nesiritide, nisoldipine, nizatidine, norfloxacin, novamine sulphone, noscapin, nystatin, ofloxacine, oktotride, olanzapine, olmesartan, olsalazine, oseltamivir, omapatrilate, omeprazole, omoconazole, ondansetrone, orlistate, oseltamivir, oxaceprol, oxacillin, oxaliplatin, oxaprozine, oxcarbacepin, oxibutin, oxicodone, oxiconazole, oxybutymin, oxycodone, oxymetazoline, palivizumab, palonosetrone, pantoprazole, paracetamol, parecoxib, paroxetine, pegaspargase, peg-interferon, pegfilgrastrim, penciclovir, oral penicillins, pentazocine, pentifylline, pentoxifylline, peptide antibiotics, perindopril, perphenazine, pethidine, plant extracts, phenazone, pheniramine, phenylbutyric acid, phenyloin, phenothiazine, phenserine, phenylbutazone, phenyloin, pimecrolimus, pimozide, pindolol, pioglitazone, piperazine, piracetam, pirenzepine, piribedil, pirlindol, piroxicam, pitavastatin, posaconazole, pramipexol, pramlintide, pravastatin, prazosine, procaine, promazine, propiverine, propranolol, propionic acid derivatives, propyphenazone, prostaglandins, protionamide, proxyphylline, quetiapine, quinapril, quinaprilate, quinupristine, rabeprazole, ramipril, ranitidine, raloxifen, ranolazine, rapamycin, rasburicase, reboxetine, repaclinide, reproterol, reserpine, revofloxacin, ribavirin, rifampicin, riluzole, rimexolone, risedronate, risperidone, ritonavir, rituximab, rivastigmine, risatriptan, rofecoxib, ropinirol, ropivacaine, rosiglitazone, rotigotine, roxatidine, roxithromycin, ruscogenin, rosuvastatin, rutoside and rutoside derivatives, sabadilla, salbutamol, salicylates, salmeterol, saperconazole, thyroid hormones, scopolamine, selegiline, sertaconazole, sertindol, sertralin, sevelamer, sibutramine, sildenafil, silicates, simvastatin, sirolimus, sitosterin, sotalol, spaglumic acid, sparfloxacin, spectinomycin, spiramycin, spirapril, spironolactone, stavudine, streptomycin, sucralfate, sufentanil, sulbactam, sulphonamides, sulphasalazine, sulpiride, sultamicillin, sultiam, sumatriptan, suxamethonium chloride, tacrin, tacrolimus, tadalafil, taliolol, talsaclidine, tamoxifen, tamsulosin, tasonermine, tazarotene, tegafur, tegaserod, telithromycin, telmisartan, temoporfin, temozolomide, tenatoprazole, tenecteplase, teniposide, tenofovir, tenoxicam, teriparatide, terazosine, terbinafine, terbutalin, terfenadine, teriparatide, terlipressin, tertatolol, testosterone and testosterone derivatives, tetracyclines, tetryzoline, tezosentan, theobromine, theophylline, theophylline derivatives, thiamazole, thiamphenicol, thiotepa, thr. growth factors, tiagabine, tiapride, tibolone, ticlopidine, tilidine, timolol, tinidazole, tioconazole, tioguanine, tiotropium, tioxolone, tirazetam, tiropramide, trofiban, tizanidine, tolazoline, tolbutamide, tolcapone, tolnaftate, tolperisone, tolterodine, topiramate, topotecan, torasemide, tramadol, tramazoline, trandolapril, tranylcypromine, trapidil, trastuzumab, travoprost, trazodone, trepostinil, triamcinolone and triamcinolone derivatives, triamterene, trifluperidol, trifluridine, trimetazidine, trimethoprim, trimipramine, tripelennamine, triprolidine, trifosfamide, tromantadine, trometamol, tropalpin, trovafloxacin, troxerutin, tulobuterol, trypsins, tyramine, tyrothricin, urapidil, ursodeoxycholic acid, theophylline ursodeoxycholic acid, valaciclovir, valdecoxib, valganciclovir, valproic acid, valsartan, vancomycin, vardenafil, vecuronium chloride, venlafaxin, verapamil, verteporfin, vidarabine, vigabatrin, viloxazine, vinblastine, vincamine, vincristine, vindesine, vinorelbine, vinpocetine, viquidil, vitamin D and derivatives of vitamin D, voriconazole, warfarin, xantinol nicotinate, ximelagatran, xipamide, zafirlukast, zalcitabin, zaleplone, zanamivir, zidovudine, ziprasidone, zoledronic acid, zolmitriptan, zolpidem, zoplicon, zotepine and the like.

If desired, the active compounds can also be used in the form of their pharmaceutically acceptable salts or derivatives, and in the case of chiral active compounds both optically active isomers and racemates or diastereomer mixtures can be employed. If desired, the compositions according to the invention can also contain two or more pharmaceutical active compounds.

Peptide or Protein Active Compounds

The pharmaceutical form according to the invention is preferably suitable for peptide or protein active compounds, which are formulated with a substance assigned to the active compound and promoting the administration of the active compound. Suitable formulations are known, for example, from WO 2005/007139.

Peptide Active Compounds Having a Molecular Weight $M_w<3000$

Abarelix, angiotensin II, anidulafimgin, antide, argipressin, azaline and azaline B, bombesin antagonist, bradykinin, buserelin, cetrorelix, ciclosporin A, desmopressin, detirelix, enkephalins (leu-, met-) ganirelix, gonadorelin, goserelin, growth hormone secretagogue, micafungin, nafarelin, leuprolide, leuprorelin, octreotide, orntide, oxytocin, ramorelix, secretin, somatotropin, terlipressin, tetracosactide, teverelix, triptorelin, thyroliberin, thyrotropin or vasopressin.

Protein or Peptide Active Compounds Having an Average Molecular Weight MW of 3000 to 10 000

Calcitonin, corticotropin, endorphins, epithelial growth factor, glucagon, insulin, novolin, parathyroid hormone, relaxin, pro-somatostatin or salmon secretin.

Protein or Peptide Active Compounds Having an Average Molecular Weight $M_w$ Over 10 000

Interferon (alpha, beta, gamma), interleukins (IL1, IL2), somatotropin, erythropoietin, tumour necrosis factor (TNF alpha, beta), relaxin, endorphin, domase alpha, follicle stimulating hormone (FSH), human chorionic gonadotropin (HCG), human growth hormone release factor (hGRF), luteinizing hormone (LH) or epidermal growth factor.

Nucleic Acid Active Compounds

The pharmaceutical form according to the invention is preferably suitable for nucleic acid active compounds which are formulated with a substance assigned to the active compound and promoting the administration of the active compound. Suitable formulations are known, for example, from WO 2006/061069.

Nucleic acid active compounds usually have the object of causing an interaction at the target site in vivo with DNA of mammalian cells, in particular human cells, which leads to a modified DNA structure in the cell or very commonly to modified cell properties. "Gene therapy" may primarily be mentioned here, whose aim is the repair of defective gene structures in genetically related diseases. This can be, for example, an inactivation or a switching off of undesired gene activities, such as, for example, the telomerase activity in tumour cells. It can also be a restoration of gene activities customarily present in healthy cells, e.g. the p53 gene activity, a long-known, intensively researched tumour suppressor gene. The invention accordingly relates to orally administrable pharmaceutical forms for nucleic acid active compounds, in particular for gene therapy.

The nucleic acid active compound can be a single- or double-stranded DNA (deoxyribonucleic acid) or RNA (ribonucleic acid) or a DNA-RNA chimera, it being possible for naturally occurring and/or not naturally occurring synthetically modified nucleotides to be contained. The nucleic acid active compound can be present in linear or cyclic form. It can be oligonucleotide units, e.g. having a length of 10 to 200 bases or base pairs. It can also be longer units of, for example, over 200 to 100 000, 500 to 10 000 or 1000 to 5 000 bases or base pairs. Besides the sequence functioning as the actual active compound, e.g. a nucleic acid sequence which is present in the target cell or is to be replaced, vector sequences can optionally also be contained in the nucleic acid active compound, which are usually not present in the target cell and should not interact with this.

Vector systems based, for example, on double-stranded DNA are known which are based on plasmids or vectors based on viral systems. Recombinant adeno-associated viral vectors (rAAV), for example, are known.

Other double-stranded vectors can contain promoter or regulation sequences from cytomegaloviruses (CMV) or the SV40 virus. Other vectors can be based on single-stranded DNA, which can be protected against degradation with the aid of attached RNA elements. Also known are "RDO I and RDO II constructs", in which short pieces of DNA, e.g. 30 to 60 bases, are provided at the end with short pieces of RNA of 1 to 4 bases. For additional increase in the half-life or the nuclease resistance, not naturally occurring nucleotides can be inserted in the RNA or DNA. Here, for example, individual oxygen atoms can be replaced by sulphur atoms, such that phosphorus-sulphur bridges are obtained (MSO). The variety of nucleic acid forms suitable as gene repair or gene replacement vectors, which can be employed as active compounds within the meaning of the present invention, is described, for example, in *Nature Reviews* Vol. 4, 2003, pp. 679-689, Li Liu et al. Nucleic acid fragments are preferred which essentially only contain the nucleic acid sequence functioning as an active compound and no or only small proportions of vector DNA.

The nucleic acid active compound can be present in a complex or conjugate, e.g. with cationic polymers or proteins such as, for example, antibodies. Complexation or conjugate bonding can take place reversibly or irreversibly by covalent means by chemical bridge bonding or by secondary valent means by Van der Waals forces, ionic bonds, hydrophobic bonding. The molecules contained in the complex or conjugate in addition to the nucleic acid active compound, however, display no therapeutic action themselves and are thus to be regarded as formulation aids and not as an active compound or parts of the active compound.

The nucleic acid active compound can optionally be formulated optionally with the aid of proteins or peptides. These, however, do not display any therapeutic action themselves and are thus to be regarded as formulation aids and not as an active compound or parts of the active compound.

The nucleic acids can be present, for example, according to WO 02/094983, in the form of a complex with an antibody which specifically binds to the nucleic acid, and of a cationic substance. It was possible to show that this measure can contribute to an increased transfection rate both in vitro and in vivo. It can be a case here preferably of monoclonal IgG antibodies or IgM antibodies, which are complete or alternatively as fragments, Fc antibody fragments, Fab' antibody fragments, F(a,b)'2 antibody fragments or half antibody fragments, but which must in each case contain at least one anti-DNA binding site. The molecular ratio of nucleic acid to anti-DNA antibody can be, for example, 1:20 to 1:5.

The nucleic acid active compound can have as its target, for example, the therapy of haemophilia and can contain a blood clotting factor gene, e.g. the cDNA gene of human blood clotting factor IX (see, for example, WO 03/028657 or Palmer et al., Blood, 1989, 73(2), pp. 438-445 or Yao et al., Proc Natl Acad Sci USA, 1992, 89(8): pp. 3357-3361). In addition to the therapeutically active gene portion, the nucleic acid active compound can also contain an immune tolerance-inducing gene, such as, for example, the Fas ligand. The co-expressed Fas ligand or gene section can initiate apoptosis in T cells, which can be specifically activated after the gene transfer to the target cells. Vectors in connection with apoptosis induction in leukaemia cells are also to be inferred from Walensky et al., 2004, *"Activation of Apoptosis in Vivo by a Hydrocarbon-Stapled BH3 Helix"*, Science, 305, pp. 1466-1470.

The nucleic acid active compound can contain, for example, a gene section, in particular the promoter region, of the human telomerase gene. The gene therapy vector pGT62-codAupp described in WO 99/38964, for example, or other vector derivable from WO 99/38964 is suitable for a person skilled in the art. The nucleic acid active compound can contain a tumor suppressor gene section, e.g. the p53 tumor suppressor gene or fragments thereof. U.S. Pat. No. 6,451,593 B1 describes construction principles for expression vectors for gene therapy, which are suitable for the preparation of nucleic acid active compounds within the meaning of the invention.

Having generally described this invention, a further understanding can be obtained by reference to certain specific examples which are provided herein for purposes of illustration only, and are not intended to be limiting unless otherwise specified.

EXAMPLES

Part A) Effects of the Partial Neutralization with Lysine

Release Test of the Theophylline Pellets According to USP 28 <711> Paddle Method (=Apparatus 2)

Process:
1. The vessels of the release apparatus were filled with 360 ml each of 0.1 M HCl (pH 1.2) and the temperature of the water bath was adjusted to 37 t 0.5° C.
2. The blade stirrer was switched on with a rate of rotation of 100 rpm.
3. 1 g of pellets was added to each vessel of the apparatus. Care was to be taken that there are no air bubbles on the pellet surface.
4. After 120 min, 140 ml of phosphate buffer solution (warmed to 37° C.) were added, such that the desired pH results in the final volume of 500 ml: pH 5.5; 5.6; 5.7; 5.8 or 7.0.
5. Determination of the time of 100% release of active compound (photometrically at 271 nm, in the recirculation procedure). For results see Table 1.

TABLE 1

Theophylline pellets having a 30% strength coating of a copolymer of 50% by weight of ethyl acrylate and 50% by weight of methacrylic acid (EUDRAGIT ® L 30 D-55), 90% of active compound released [min], process according to USP 28 paddle

|  | Example A1 15% partial neutralization with lysine | | Example A2 15% partial neutralization with NaOH | | Example A3 no partial neutralization | |
|---|---|---|---|---|---|---|
| previously 2 h, pH 1.2 | + | − | + | − | + | − |
| pH 5.5 | 45 | 40 | 90 | 45 | 120 | 120 |

TABLE 1-continued

Theophylline pellets having a 30% strength coating of a copolymer of 50% by weight of ethyl acrylate and 50% by weight of methacrylic acid (EUDRAGIT ® L 30 D-55), 90% of active compound released [min], process according to USP 28 paddle

|        | Example A1 15% partial neutralization with lysine | | Example A2 15% partial neutralization with NaOH | | Example A3 no partial neutralization | |
|--------|----|----|----|----|----|----|
| pH 5.6 | 30 | 28 | 50 | 30 | 60 | 60 |
| pH 5.7 | 20 | 19 | 30 | 20 | 50 | 50 |
| pH 5.8 | 18 | 17 | 20 | 18 | 30 | 30 |
| pH 7.0 | Immediate release of active compound | | | | | |

Example A1

Formulation with Lysine

Pellet coatings with EUDRAGIT L 30 D 55 (30% strength dispersion, comprising a copolymer of 50% by weight of ethyl acrylate and 50% by weight of methacrylic acid) partially neutralized with lysine. 30% of dry matter of a polymer dispersion (methacrylate copolymer of 50% by weight of methacrylic acid and 50% by weight of ethyl acrylate) was coated onto 100 g of theophylline pellets, from Klinge Pharma, having the particle size of 0.7-1.0 mm using the following formulations. The total dry content application was 35.7% by weight based on the batch amount.

For release investigation of 90% by weight of the active compound see Table 1.

| Materials | (g) |
|---|---|
| EUDRAGIT ® L 30 D-55 | 100.00 |
| Lysine | 3.69 |
| Glyceryl monostearate | 1.50 |
| Polysorbate 80 | 0.60 |
| Water dem. | 132.81 |
| Total | 238.60 |

Spray parameters in the Hüttlin Mycrolab:

| | |
|---|---|
| Spray nozzle | 0.6 mm |
| Spray rate | 26 g/min/kg |
| Spray pressure | 1.0 bar |
| Microclimate | 0.6 bar |
| Feed air airflow | 20 m³ |
| Feed air temperature | 33-39° C. |
| Product temperature | 26-29° C. |
| After drying time in the apparatus | 10 min at 40° C. |
| Spraying time | 1.5-2 h |
| Drying overnight at | room temperature (RT) |

Example A2

Formulation with NaOH

Pellet coating with EUDRAGIT® L 30 D 55 partially neutralized with NaOH. 30% of dry matter of a polymer dispersion (methacrylate copolymer of 50% by weight of methacrylic acid and 50% by weight of ethyl acrylate) was coated onto 100 g of theophylline pellets, from Klinge Pharma, having the particle size of 0.7-1.0 mm using the following formulations. The total dry content application was 33.11% by weight based on the batch amount.

For the release investigation of 90% by weight of the active compound see Table 1.

| Materials | (g) |
|---|---|
| EUDRAGIT ® L 30 D-55 | 100.00 |
| NaOH | 1.01 |
| Glyceryl monostearate | 1.50 |
| Polysorbate 80 | 0.60 |
| Water dem. | 117.62 |
| Total | 220.73 |

Spray parameters in the Huttlin Mycrolab:

| | |
|---|---|
| Spray nozzle | 0.6 mm |
| Spray rate | 27 g/min/kg |
| Spray pressure | 1.0 bar |
| Microclimate | 0.6 bar |
| Feed air airflow | 20 m³ |
| Feed air temperature | 33-40° C. |
| Product temperature | 26-30° C. |
| After drying time in the apparatus | 10 min at 40° C. |
| Spraying time | 1-1.5 h |
| Drying overnight at room temperature | |

Example A3

Formulation without Partial Neutralization

Pellet coating with EUDRAGIT L 30 D 55 without partial neutralization.

30% of dry matter of a polymer dispersion (methacrylate copolymer of 50% by weight of methacrylic acid and 50% by weight of ethyl acrylate) was coated onto 100 g of theophylline pellets, from Klinge Pharma, having the particle size of 0.7-1.0 mm using the following formulations. The total dry content application was 32.111% by weight based on the batch amount.

For release investigation of 90% by weight of the active compound see Table 1.

| Materials | (g) |
|---|---|
| EUDRAGIT ® L 30 D-55 | 100.00 |
| Glyceryl monostearate | 1.50 |
| Polysorbate 80 | 0.60 |
| Water dem. | 136.83 |
| Total | 238.93 |

Spray parameters in the MiniGlatt:

| | |
|---|---|
| Spray nozzle | 0.5 mm |
| Spray rate | 1-2 g/min |
| Spray pressure | 0.8 bar |
| Feed air | 0.7 bar |
| Feed air temperature | 35-37° C. |

-continued

| | |
|---|---|
| Product temperature | 32-33° C. |
| After drying time in the apparatus | 10 min at 40° C. |
| Spraying time | about 2-3 h |
| Drying overnight at | room temperature |

Part B) Pharmaceutical Forms Having a Three-Layer Separating Layer and Polymer Coatings Optionally Partially Neutralized with Lysine Preparation of the Coatings Theophylline pellets of 710-1250 μm from Klinge Pharma having a 94.13% theophylline content were employed as a starting material for all coatings.

Example B1

Comparison, not According to the Invention

Standard EUDRAGIT® L 30 D-55 formulation:
15.0% strength of dry matter were sprayed onto 100 g of theophylline pellets, 710-850 μm, in the Huttlin Mycrolab using an aqueous spray suspension. Composition of the suspension: 66.7 g of EUDRAGIT® L 30 D-55, 2.0 g of triethyl citrate, 1.5 g of glyceryl monostearate, 0.6 g of polysorbate 80. The release of active compound of these pellets according to USP No 2 (paddle) and residual active compound content after 2 hours in 0.1 N HCl and subsequently phosphate buffer pH 5.8 was:

| | Time | | |
|---|---|---|---|
| | 120 min | 140 min | 145 min |
| Layer thickness MW total after gastric juice [μm] | 29-38 | 18-25 | 0-9 |
| Residual active compound in formulation [%] | 99.5 | 90.5 | 78.3 |

Example B2

Comparison, not According to the Invention

Formulation containing EUDRAGIT® L 30 D-55 and lysine 15% strength partially neutralized:
15.0% strength of dry matter were sprayed onto 100 g of theophylline pellets, 710-850 pm, in the Hüttlin Mycrolab using an aqueous spray suspension. Composition of the suspension: 66.7 g of EUDRAGIT® L 30 D-55, 2.5 g of lysine, 2.0 g of triethyl citrate, 1.5 g of glyceryl monostearate, 0.6 g of polysorbate 80. The release of active compound and residual active compound content of these pellets according to USP No. 2 (paddle) for 2 hours in 0.1 N HCl and subsequently phosphate buffer pH 5.8 was:

| | Time | | |
|---|---|---|---|
| | 120 min | 140 min | 145 min |
| Layer thickness MW total after gastric juice [μm] | 18-38 | 19-33 | 9-35 |
| Residual active compound in formulation [%] | 93.7 | 71.0 | 56.4 |

Example B3

Comparison, not According to the Invention

Formulation containing EUDRAGIT® L 30 D-55 and HPMC as a single-layer separating layer:
A.) 10.0 g of HPMC (Methocel E 5) were dissolved in 132.9 g of dem. water. Spray application was carried out on 100 g of theophylline pellets, 710-850 pm, in the Hüttlin Mycrolab.

Subsequently, the spray suspension from Example 1 was sprayed onto 100 g of the pellets from A.).

The release of active compound and residual active compound content of these pellets according to USP No. 2 (paddle) for 2 hours in 0.1 N HCl and subsequently phosphate buffer pH 5.8 was:

| | Time | | |
|---|---|---|---|
| | 120 min | 140 min | 145 min |
| Layer thickness MW total after gastric juice [μm] | 24-35 | 8-15 | 0 |
| Residual active compound in formulation [%] | 99.4 | 81.0 | 36.6 |

Example B4

According to the Invention

Formulation containing EUDRAGIT® L 30 D-55 and HPMC/capric acid/HPMC as a three-layer separating layer:
B.) 5.0 g of HPMC (Methocel E 5) were dissolved in 66.4 g of dem. water and sprayed onto 100 g of theophylline pellets, 710-8501, in the Huttlin Mycrolab.

C.) 5.0 g of capric acid were dissolved in 61.7 g of abs. ethanol and sprayed onto 100.0 g of pellets from B.), likewise in the Hüttlin Mycrolab.

D.) 5.0 g of HPMC (Methocel E 5) were dissolved in 66.4 g of dem. water and again sprayed onto 100 g of pellets from C.).

Subsequently, the spray suspension from Example 1 was applied to 100 g of pellets D.).

The release of active compound and residual active compound content of these pellets according to USP No 2 (paddle) 2 hours in 0.1 N HCl and subsequently phosphate buffer pH 5.8 was:

|  | Time | | |
|---|---|---|---|
|  | 120 min | 140 min | 145 min |
| Layer thickness MW total after gastric juice [μm] | 34-51 | 4-19 | 0-12 |
| Residual active compound in formulation [%] | 99.4 | 93.6 | 80.4 |

Example B5

Not According to the Invention

Formulation containing EUDRAGIT® L 30 D-55 partially neutralized with 15% lysine and HPMC as a single-layer separating layer:

A.) 10.0 g of HPMC (Methocel E 5 Premium) were dissolved in 132.9 g of dem. water and subsequently sprayed onto 100 g of theophylline pellets, 710-850 μm, in the Huttlin Mycrolab.

Subsequently, the spray suspension of Example 2 was applied to 100 g of pellets A.)

The release of active compound and residual active compound content of these pellets according to USP No 2 (paddle) 2 hours in 0.1 N HCl and subsequently phosphate buffer pH 5.8 was:

|  | Time | | |
|---|---|---|---|
|  | 120 min | 140 min | 145 min |
| Layer thickness MW total after gastric juice [μm] | 21-42 | 5-20 | 0-18 |
| Residual active compound in formulation [%] | 97.2 | 43.1 | 20.9 |

Example B6

According to the Invention

Formulation containing EUDRAGIT® L 30 D-55 partially neutralized with 15% lysine and HPMC/capric acid/HPMC as a three-layer separating layer:

B.) 5.0 g of HPMC (Methocel E 5 Premium) were dissolved in 66.4 g of dem. water and sprayed onto 100 g of theophylline pellets, 710-1250 μm, in the Hüttlin Mycrolab.

C.) 5.0 g of capric acid were dissolved in 61.7 g of abs. ethanol and sprayed onto 100.0 g pellets from B.), likewise in the Hüttlin.

D.) 5.0 g of HPMC (Methocel E 5 Premium) were dissolved in 66.4 g of dem. water and again sprayed onto 100 g of pellets from C.).

Subsequently, the spray suspension from Example 2 was sprayed onto 100 g of pellets D.).

The release of active compound and residual active compound content of these pellets according to USP No 2 (paddle) for 2 hours in 0.1 N HCl and subsequently phosphate buffer pH 5.8 was:

|  | Time | | |
|---|---|---|---|
|  | 120 min | 140 min | 150 min |
| Layer thickness MW total after gastric juice [μm] | 24-38 | 0 | 0 |
| Residual active compound in formulation [%] | 97.3 | 81.7 | 16.6 |

Film Detachment Test.

250 mg each of the pellets from Examples B1-B6 were stirred in 700 ml of 0.1 N HCl for 2 hours according to USP No. 2 (paddle) and subsequently adjusted to pH 5.8 with Na$_3$PO$_4$ solution. Sampling of about 10 pellets was carried out after 120 min (before rebuffering), after 140, 145 min, and after 150 min (phosphate buffer pH 5.8).

The moist pellets were laid on an absorbent tissue and dried at RT. Subsequently, the surface and fragments of the pellets were investigated under the scanning electron microscope (REM) and the remaining layer thickness was determined.

Evaluation of the Residual Active Compound Content Versus Layer Thickness:

|  | Standard L30 D-55 | partially neutralized L30 D-55 | HPMC + standard L30 D-55 | 3-layer + standard L30 D-55 | HPMC + partially neutr. L30 D-55 | 3-layer + partially neutr. L30 D-55 |
|---|---|---|---|---|---|---|
|  | | | | Example | | |
|  | B1 | B2 | B3 | B4 | B5 | B6 |
| Partially neutralized with lysine | − | + | − | − | + | + |
| 1-layer | − | − | + | − | + | − |
| 3-layer | − | − | − | + | − | + |
| EUDRAGIT ® L 30 D-55 layer thickness after rebuffering for 20 min | +++ | +++ | ++ | ++ | ++ | + |
| Residual active compound in formulation after 140 min, (20 min after rebuffering) in [%] | 90.5 | 71.0 | 81.0 | 93.6 | 43.1 | 81.7 |

+ = no EUDRAGIT ® L30 D-55 layer (0 to less than 5 μm)
++ = thin EUDRAGIT ® L 30 D-55 layer (from 5 to about 20 μm)
+++ = thick EUDRAGIT ® L30 D-55 layer (greater than 20-about 45 μm)

German patent application 10 2006 035 459.0 filed Jul. 27, 2006 and U.S. provisional application Ser. No. 60/908,855 are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A pharmaceutical form, comprising:
an active compound-containing core, which is covered with a coating layer of a gastric juice-resistant, intestinal juice-soluble (meth)acrylate copolymer,
a separating layer situated between said core and said coating layer,
said separating layer comprising a film-forming water-soluble polymer,
wherein the separating layer comprises at least two layers:
an inner layer which rapidly detaches from the core in micellar form under physiological conditions from pH 5.5 and consists essentially of a water-repellent substance selected from the group consisting of a $C_8$- to $C_{24}$-fatty alcohol, an ester of a $C_8$- to $C_{24}$-fatty alcohol with an organic acid, a $C_8$- to $C_{24}$-fatty acid, an ester of a $C_8$- to $C_{24}$-fatty acid with an alcohol, an ester of a $C_8$- to $C_{24}$-fatty acid with a polyol, and mixtures thereof, and
thereon a layer comprising the film-forming water-soluble polymer;
wherein said inner layer is formed of water-repellent substance which is not a polymer.

2. The pharmaceutical form according to claim 1, wherein said separating layer comprises three layers:
two layers of the film-forming water-soluble polymer enclosing a layer containing the water-repellent substance.

3. The pharmaceutical form according to claim 1, wherein said film-forming, water-soluble polymer comprises a member selected from the group consisting of non-ionic cellulose derivatives, polysaccharides, polyethylene glycols, polyvinylpyrrolidone and mixtures thereof.

4. The pharmaceutical form according to claim 3, wherein the film-forming, water-soluble polymer is a hydroxypropylmethylcellulose having a viscosity of 1 to 20 mPa·s, based on a 1% strength aqueous solution (weight/weight).

5. The pharmaceutical form according to claim 1, comprising 1 to 50% by weight of said layer comprising said film-forming, water-soluble polymer, based on the weight of the active compound-containing core.

6. The pharmaceutical form according to claim 1, comprising 0.1 to 25% by weight of the layer of the water-repellent substance, based on the weight of the active compound-containing core.

7. The pharmaceutical form according to claim 1, wherein the film-forming, water-soluble polymer has a solubility in demineralized water of at least 50 g/l at 20° C.

8. The pharmaceutical form according to claim 1, wherein the water-repellent substance has a solubility in acetone of at least 50 g/l at 20° C.

9. The pharmaceutical form according to claim 1, wherein the gastric juice-resistant, intestinal juice-soluble polymer coating is an anionic (meth)acrylate copolymer, comprising free radical-polymerized units of
(i) 25 to 95% by weight of $C_1$- to $C_4$-alkyl esters of acrylic or of methacrylic acid, and
(ii) 5 to 75% by weight of (meth)acrylate monomers having an anionic group.

10. The pharmaceutical form according to claim 9, wherein the anionic (meth)acrylate copolymer comprises free radical-polymerized units of
(i) 40 to 60% by weight of methacrylic acid, and
(ii) 60 to 40% by weight of methyl methacrylate or ethyl acrylate.

11. The pharmaceutical form according to claim 9, wherein the anionic (meth)acrylate copolymer of the coating is entirely or proportionately partially neutralized, using a base.

12. The pharmaceutical form according to claim 11, wherein 0.1 to 25% of the anionic groups of the (meth)acrylate copolymer are neutralized.

13. The pharmaceutical form according to claim 11, wherein the base is a cationic, organic base having a molecular weight of over 150, or lysine.

14. The pharmaceutical form according to claim 13, wherein the base is histidine, arginine, a polyhistidine, a polyarginine, a polylysine, a phospholipid, a base of a cationic surface-active excipient, an emulsifier or mixtures thereof.

15. The pharmaceutical form according to claim 13, wherein (i) arginine or (ii) lysine and arginine are used as partial neutralizing agents.

16. The pharmaceutical form according to claim 13, wherein the polymer coating comprises lysine and/or arginine in combination with 5 to 25% by weight of a plasticizer based on the weight of the polymer in said coating.

17. The pharmaceutical form according to claim 13, wherein the polymer coating comprises lysine and/or arginine in a concentration of 10 to 30% by weight based on the polymer in said coating.

18. The pharmaceutical form, according to claim 1, wherein the core comprises
an active compound, and
a substance promoting the administration of the active compound.

19. The pharmaceutical form according to claim 18, wherein the active compound is a peptide, a protein, a nucleic acid, a polysaccharide, a derivative of a peptide, a derivative of a protein, a derivative of a nucleic acid, a derivative of a polysaccharide or mixtures thereof.

20. The pharmaceutical form according to claim 18, wherein the substance promoting the administration of the active compound is a penetration promoter, a mucoadhesive polymer, a substance which inhibits the enzymatic degradation of the active compound by enzymes occurring in the digestive tract, an efflux pump inhibitor or mixtures thereof.

21. The pharmaceutical form according to claim 1, which is present in the form of a multiparticulate of pellet-containing tablets, minitablets, capsules, sachets, effervescent tablets or inspissated juices.

22. The pharmaceutical form according to claim 1, wherein the water-repellent substance has a melting point in the range from 30 to 40° C.

23. The pharmaceutical form according to claim 1, wherein the water-repellent substance is selected from the group consisting of stearic acid, capric acid, glycerol monostearate, and glycerol distearate.

24. The pharmaceutical form according to claim 1, comprising 3 to 8% by weight of the layer of the water-repellent substance, based on the weight of the active compound-containing core.

25. A pharmaceutical form, comprising:
an active compound-containing core, which is covered with a coating layer of a gastric juice-resistant, intestinal juice-soluble (meth)acrylate copolymer, and a separating layer situated between said core and said coating layer;

wherein said separating layer comprises at least two layers;

wherein a water-repellent substance which is not a polymer and consists essentially of a substance selected from the group consisting of a $C_8$- to $C_{24}$-fatty alcohol, an ester of a $C_8$- to $C_{24}$-fatty alcohol with an organic acid, a $C_8$- to $C_{24}$-fatty acid, an ester of a $C_8$- to $C_{24}$-fatty acid with an alcohol, an ester of a $C_8$- to $C_{24}$-fatty acid with a polyol, and mixtures thereof forms an inner layer of said at least two layers, wherein the inner layer rapidly detaches from the core in micellar form under physiological conditions from pH 5.5, and wherein a film-forming water-soluble polymer forms the outer layer of said at least two layers.

26. The pharmaceutical form according to claim 1, wherein said separating layer comprises three layers:

two layers of the film-forming water-soluble polymer enclosing a layer formed of the water-repellent substance which is not a polymer.

27. The pharmaceutical form according to claim 1, comprising 1 to 25% by weight of the layer of the water-repellent substance, based on the weight of the active compound-containing core.

* * * * *